(12) United States Patent
Boenitz-Dulat et al.

(10) Patent No.: US 7,547,524 B2
(45) Date of Patent: Jun. 16, 2009

(54) GENETICALLY ENGINEERED PYRROLOQUINOLINE QUINONE DEPENDENT GLUCOSE DEHYDROGENASE COMPRISING AN AMINO ACID INSERTION

(75) Inventors: Mara Boenitz-Dulat, Tutzing (DE); Jessica Laggerbauer, München (DE); Rainer Schmuck, Benediktbeuern (DE); Peter Kratzsch, Penzberg (DE); Wolfgang-Reinhold Knappe, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/632,672

(22) PCT Filed: Jul. 19, 2005

(86) PCT No.: PCT/EP2005/007844
§ 371 (c)(1),
(2), (4) Date: Jan. 17, 2007

(87) PCT Pub. No.: WO2006/008132
PCT Pub. Date: Jan. 26, 2006

(65) Prior Publication Data
US 2007/0243566 A1    Oct. 18, 2007

(30) Foreign Application Priority Data
Jul. 20, 2004    (EP)    .................. 04017069

(51) Int. Cl.
*C12Q 1/32*    (2006.01)
*C12N 9/02*    (2006.01)

(52) U.S. Cl. ........................................ 435/26; 435/189
(58) Field of Classification Search .................. 435/26, 435/189
See application file for complete search history.

(56) References Cited

U.S. PATENT DOCUMENTS

| | | | |
|---|---|---|---|
| 5,484,708 A | 1/1996 | Hoenes et al. | |
| 5,997,817 A | 12/1999 | Crismore et al. | |
| 6,057,120 A | 5/2000 | Heindl et al. | |
| 6,103,509 A | 8/2000 | Sode | |

FOREIGN PATENT DOCUMENTS

| | | |
|---|---|---|
| EP | 0620283 B1 | 9/1998 |
| EP | 1167519 A1 | 1/2002 |
| EP | 1176202 A1 | 1/2002 |
| EP | 1367120 A2 | 12/2003 |
| JP | 11-243949 | 9/1999 |
| JP | 2004-173538 | 6/2004 |
| WO | WO88/09373 | 12/1988 |
| WO | WO02/34919 A1 | 5/2002 |

OTHER PUBLICATIONS

Inference of protein function from protein structure; Pal et al. Structure 2004, 13, pp. 121-130.*
Anthony, Christopher, "Quinoprotein-Catalysed Reactions," Biochem. Journal, 1996, vol. 320, pp. 697-711.
Anthony, Christopher, et al., "The Structure and Function of PQQ-Containing Quinoproteins," Current Science, 1997, vol. 72, pp. 716-727.
Anthony, Christopher, et al., "The Structure and Function of the PQQ-Containing Quinoprotein Dehydrogenases," Progress in Biophysics & Molecular Biology, 1998, vol. 69, pp. 1-21.
Anthony, Christopher, "The Pyrroloquinoline Quinone (PQQ)-Containing Quinoprotein Dehydrogenases," Biochemical Society Transactions, 1998, vol. 26, pp. 413-417.
Anthony, Christopher, "The Pyrroloquinoline Quinone (PQQ)-Containing Dehydrogenases," Respiration in Archaea and Bacteria, 2004, vol. 1, pp. 203-225.
Ausubel, Frederick M., et al., "Current Protocols in Molecular Biology," Wiley, 2001, vol. 1.
Cleton-Jansen, Anne Marie, et al., "Cloning of the Genes Encoding the Two Different Glucose Dehydrogenases From Acinetobacter Calcoaceticus," Antonie van Leeuwenhock, 1989, No. 56, pp. 73-79.
Cleton-Jansen, Anne Marie, et al., "Cloning of the Gene Encoding Quinoprotein Glucose Dehydrogenase From Acinetobacter Calcoaceticus: Evidence for the Presence of a Second Enzyme," Journal Of Bacteriology 1988, vol. 170, No. 5, pp. 2121-2125.
Cleton-Jansen, Anne Marie, et al., "Cloning, Characterization and DNA Sequencing of the Gene Encoding the Mr 50 000 Quinoprotein Glucose Dehydrogenase from Acinetobacter Calcoaceticus," Mol. Gen. Genet. 1989, No. 217, pp. 430-436.
Davidson, Victor L., "Principles and Applications of Quinoproteins," whole book, 1993, Marcel Dekker, Inc. New York.
Davies, Donald S., "Kinetics of Icodextrin," Peritoneal Dialysis International, 1994, vol. 14, Suppl. 2, pp. 45-50.
D'Costa, E.J., et al., "Quinoprotein Glucose Dehydrogenase and its Application in an Amperometric Glucose Sensor," Biosensors 2, 1986, pp. 71-87.
Dokter, P., et al., "The In Vivo and In Vitro Substrate Specificity of Quinoprotein Glucose Dehydrogenase of Acinetobacter Calcoaceticus LMD79.41," FEMS Microbiology Letters 43, 1987, pp. 195-200.
Dokter, P., et al., "Purification and Characterization of Quinoprotein Glucose Dehydrogenase from Acinetobacter Calcoaceticus L.M.D. 79.41," Biochem J., 1986, No. 239, pp. 163-167.
Dokter, P., et al., "Cytochrome b-562 from Acinetobacter Calcoaceticus L.M.D. 79.41," Biochem J., 1988, No. 254, pp. 131-138.

(Continued)

*Primary Examiner*—Tekchand Saidha
(74) *Attorney, Agent, or Firm*—Barnes & Thornburg LLP

(57) ABSTRACT

The present invention relates to improved variants of soluble pyrroloquinoline quinone (PQQ)-dependent glucose dehydrogenases (s-GDH) comprising an amino acid insertion between positions 428 and 429 as corresponding to the amino acid sequence known from *Acinetobacter calcoaceticus*, to genes encoding such variant s-GDH, to proteins of such s-GDH variants with improved substrate specificity for glucose, and to different applications of these s-GDH variants, particularly for determining concentrations of sugars, especially of glucose in a sample.

13 Claims, 4 Drawing Sheets

OTHER PUBLICATIONS

Figure 2:
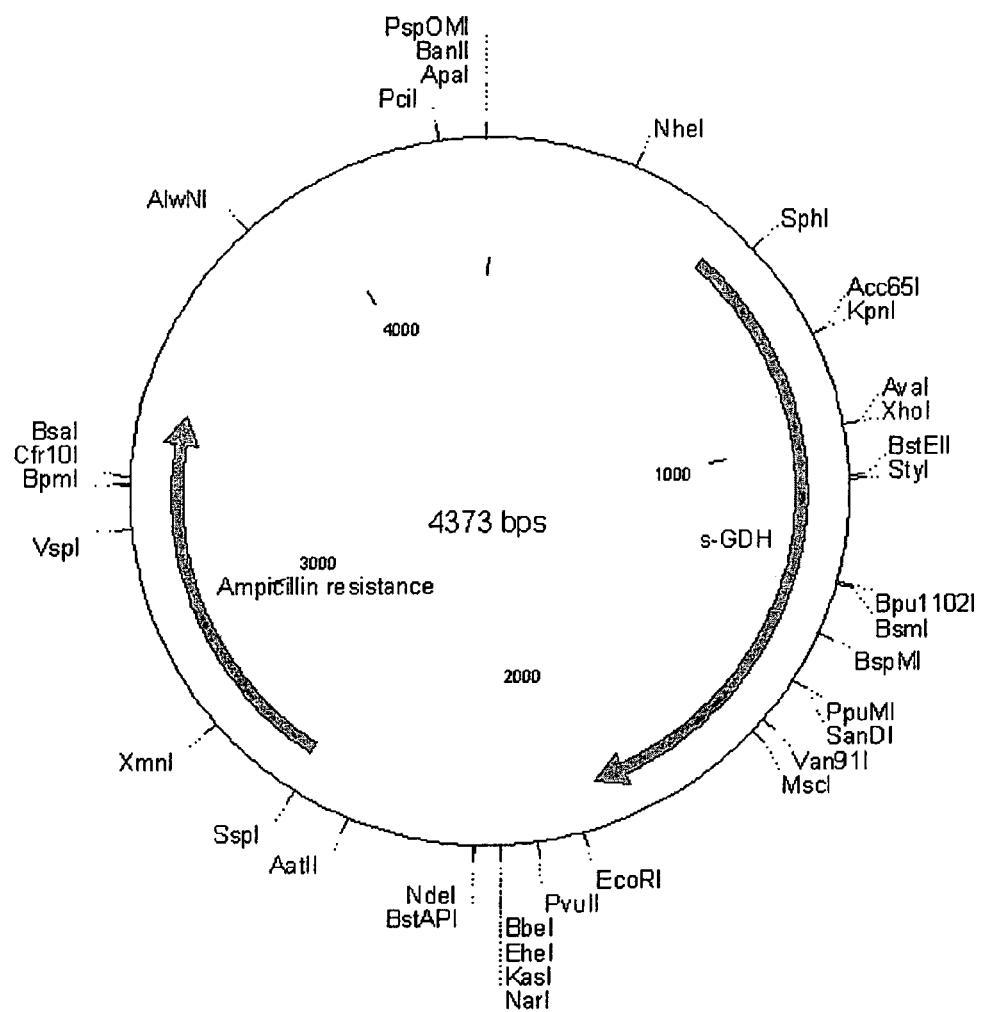

Duine, J.A., "Energy Generation and the Glucose Dehydrogenase Pathway in Acinetobacter," The Biology of Acinetobacter, 1991, Plenum Press, New York, pp. 295-312.

Duine, J.A., "The Importance of Natural Diversity in Redox Proteins for Achieving Cofactor-Electrode-Directed Electron Transfer," Biosensors & bioelectronics, 1995, No. 10, pp. 17-23.

Duine, J.A., "Quinoproteins: Enzymes Containing the Quinonoid Cofacter Pyrroloquinoline Quinone, Topaquinone or Trypotphan-Tryptophan Quinone," Eur. J. Biochem., 1991, No. 200, pp. 271-284.

Feng, Da-Fei, et al., "Progressive Sequence Alignment as a Prerequisite to Correct Phylogenetic Trees," Journal of Molecular Evolution, 1987, No. 25, pp. 351-360.

Frampton, James E., et al., "Icodextrin A Review of its Use in Peritoneal Dialysis," Adis Drug Evaluation., 2003, vol. 63, No. 19, pp. 2079-2105.

Goodwin, Pat M., et al., "The Biochemistry, Physiology and Genetics of PQQ and PQQ-Containing Enzymes," Advances In Microbial Physiology, 1998, vol. 40, pp. 1-80.

Hill, David E., et al., "Mutagenesis with Degenerate Oligonucleotides: An Efficient Method for Saturating a Defined DNA Region with Base Pair Substitutions," Methods In Enzymology, 1987, vol. 155, pp. 558-568.

Igarashi, Satoshi, et al., "Construction and Characterization of Mutant Water-Soluble PQQ Glucose Dehydrogenase with Altered Km Values-Site-Directed Mutagenesis Studies on the Putative Active Site," Biochemical and Biophysical Research Communications, 1999, No. 264, pp. 820-824.

Kaufman, Norbert, et al., "Glucotrend," "Development and Evaluation of a New System for Determining Glucose From Fresh Capillary Blood Heparinised Venous Blood," Boehringer Mannheim GmbH, 1997, pp. 1-16.

Kim, Chul Hong, et al., "Closing and Expression of Pyrroloquinoline Quinone (PQQ) Genes From a Phosphate_Solubilizing Bacterium Enterobacter intermedium," Current Microbiology, 2003, vol. 47, pp. 457-461.

Laurinavicius, V., et al., "Oxygen Insensitive Glucose Biosensor Based On PQQ-Dependent glucose Dehydrogenase," Analytical Letters, 1999, vol. 32, No. 2, pp. 299-316.

Laurinavicius, V., et al., "A Novel Application of Heterocyclic Compounds for Biosensors Based on NAD, FAD, PQQ Dependent Oxidoreductases," Chemical Monthly, 1999, No. 130, pp. 1269-1281.

Laurinavicius, V., et al., "Comparative Characterization of Soluble and Membrane-Bound PQQ-Glucose Dehydrogenases," Institute of Biochemistry, 2003, pp. 31-34.

Leung, David W., et al., "A Method For Random Mutagenesis of A Defined DNA Segment Using A Modified Polymerase Chain Reaction", The Department of Microbiology, Genentech, Inc., 1989, pp. 11-15.

Matsushita, Kazunobu, et al., "Quinoprotein D-glucose Dehydrogenase in Acinetobactor Calcoaceticus LMD 79.41: Purification and Characterization of the Membrane-Bound Enzyme Distinct from the Soluble Enzyme," Antonie van Leeuwenhoek, 1989, No. 56, pp. 63-72.

Matsushita, Kazunobu, et al., "Quinoprotein D-glucose Dehydrogenase of the Acinetobactor calcoaceticus Respiratory Chain: Membrane-Bound and Soluble Forms are Different Molecular Species," Biochemistry, 1989, No. 28, pp. 6276-6280.

Matsushita, Kazunobu, et al., "Soluble and Membrane-Bound Quinoprotein D-Glucose Dehydrogenase of the Acinetobacter calcoaceticus: The Binding Process of PQQ to the Apoenzymes," Bioscience Biophysics Biochem., 1995, No. 59, pp. 1548-1555.

Olsthoorn, Arjen J.J., et al., "Production, Characterization, and Reconstruction of Recombinant Quinoprotein Glucose Dehydrogenase (Soluble Type; EC 1.199.17) A poenzyme of Acinetobacter Calcoaceticus," Archives of Biochemistry and Biophysics, 1996, vol. 336, No. 1, Article No. 0530, pp. 42-48.

Olsthoorn, Arjen J.J., et al., "On the Mechanism and Specificity of Soluble, Quinoprotein Glucose Dehydrogenase in the Oxidation of Aldose Sugars," Biochemistry, 1998, No. 37, pp. 13854-13861.

Oubrie, Arthur, "Structure and Mechanism of Soluble Glucose Dehydrogenase and Other PQQ-Dependent Enzymes," Biochemistry and Biophysica, 2003, No. 1647, pp. 143-151.

Oubrie, Arthur, et al., "Structural Requirements of Pyrroloquinoline Quinone Dependent Enzymatic Reactions (In Process Citation)," Protein Science, 2000, No. 9, pp. 1265-1273.

Oubrie, Arthur, et al., "Structure and Mechanism of Soluble Quinprotein Glucose Dehydrogenase," European Molecular Biology Org., 1999, vol. 18, No. 19, pp. 5187-5194.

Oubrie, Arthur, et al., "The 1.7 A Crystal Structure of the Apo Form of the Soluble Quinoprotein Glucose Dehydrogenase from Acinetobacter calcoaceticus Reveals a Novel Internal Conserved Sequence Repeat," Laboratory of Biophysical Chemistry and BIOSON, 1999, No. 289, pp. 319-333.

Oubrie, Arthur, et al. "Active-Site Structure of the Soluble Quinoprotein Glucose Dehydrogenase Complexed with Methylhydrazine: A Covalent Cofactor-Inhibitor Complex," Laboratory of Biophysical Chemistry and BIOSON, 1999, vol. 96, No. 21, pp. 11787-11791.

Reddy, Swarnalath, et al., "Mechanism of Glucose Oxidation by Quinoprotein Soluble Glucose Dehydrogenease: Insights from Molecular Dynamics Studies," American Chemical Society, 2004, No. 126, pp. 2431-2438.

Sambrook, J., et al., "Molecular Cloning-A Laboratory Manual ," Cold Spring Harbor Laboratory Press, 1989, whole book.

Sode, Koji, et al., "Construction of Engineered Water-Soluble PQQ Glucose Dehydrogenase with Improved Substrate Specificity," Department of Biotechnology, 2002, pp. 405-412.

Wens, Robert, et al., "A Previously Undescribed Side Effect of Icodextrin: Overestimation of Glycemia by Glucose Analyzer," Department of Nephrology, 1998, pp. 603-609.

Yamada, Mamoru, et al., "*Escherichia coli* PQQ-Containing Quinoprotein Glucose Dehydrogenase its Structure Comparison with Other Quinoproteins," Ciochemica et Biophysica Acta, 2003, No. 1647, pp. 185-192.

Ye, Ling, et al., "High Current Density "Wired" Quinoprotein Glucose Dehydrogenase Electrode," American Chemical Society, 1993, No. 65, pp. 238-241.

* cited by examiner

Fig. 1

Amino acid sequences of A. calcoaceticus (top) and
          A. baumannii (bottom)

```
  1 DVPLTPSQFAKAKSENFDKKVILSNLNKPHALLWGPDNQIWLTERATGKI  50
    |:||||.||||||.|||||||||||||||||||||||||||||||||||
  1 DIPLTPAQFAKAKTENFDKKVILSNLNKPHALLWGPDNQIWLTERATGKI  50

51 LRVNPESGSVKTVFQVPEIVNDADGQNGLLGFAFHPDFKNNPYIYISGTF 100
    |||||  |||  |||||||||||.|||||||||||||||||.|||||||||
 51 LRVNPVSGSAKTVFQVPEIVSDADGQNGLLGFAFHPDFKHNPYIYISGTF 100

101 KNPKSTDKELPNQTIIRRYTYNKSTDTLEKPVDLLAGLPSSKDHQSGRLV 150
    |||||||||||||||||||||||.|||  |||:||:|||||||||||||
101 KNPKSTDKELPNQTIIRRYTYNKTTDTFEKPIDLIAGLPSSKDHQSGRLV 150

151 IGPDQKIYYTIGDQGRNQLAYLFLPNQAQHTPTQQELNGKDYHTYMGKVL 200
    |||||||||||||||||||||||| |||||||||||| ||||||||||||
151 IGPDQKIYYTIGDQGRNQLAYLFLSNQAQHTPTQQELNSKDYHTYMGKVL 200

201 RLNLDGSIPKDNPSFNGVVSHIYTLGHRNPQGLAFTPNGKLLQSEQGPNS 250
    |||||||||||||||||||||||||||||||||| |||||||||||||||
201 RLNLDGSIPKDNPSFNGVVSHIYTLGHRNPQGLAFAPNGKLLQSEQGPNS 250

251 DDEINLIVKGGNYGWPNVAGYKDDSGYAYANYSAAANKS.IKDLAQNGVK 299
    ||||||:.||||||||||||||||||||||||||||| ||| |||||||:|
251 DDEINLVLKGGNYGWPNVAGYKDDSGYAYANYSAATNKSQIKDLAQNGIK 300

300 VAAGVPVTKESEWTGKNFVPPLKTLYTVQDTYNYNDPTCGEMTYICWPTV 349
    || |||||||||||||||||||||||||||||||||||||||| |||||||
301 VATGVPVTKESEWTGKNFVPPLKTLYTVQDTYNYNDPTCGEMAYICWPTV 350

350 APSSAYVYKGGKKAITGWENTLLVPSLKRGVIFRIKLDPTYSTTYDDAVP 399
    ||||||||  |||||| |||||||||||||||||||||||||||| |||:|
351 APSSAYVYTGGKKAIPGWENTLLVPSLKRGVIFRIKLDPTYSTTLDDAIP 400

400 MFKSNNRYRDVIASPDGNVLYVLTDTAGNVQKDDGSVTNTLENPGSLIKF 449
    ||||||||||||||:|| ||||||||||||||||||||.|||||||||||
401 MFKSNNRYRDVIASPEGNTLYVLTDTAGNVQKDDGSVTHTLENPGSLIKF 450

450 TYKAK 454
    || |
451 TYNGK 455
```

Fig. 3a

Sequence vector pACSGDH

```
cactaactga ttacgcaccg catgtaaccg ttttcaatct gtgagtaaat tcacagttta   60
ttaacattgt gatagctatg atgacaacgt ttgtcgcact gtaactaacg tgtaacagtt  120
agttgtcagt tttgctgggg tatttcgctt ataaaaaccg ttatcacaat atcccgcgac  180
taccggacaa aaataaagag ttgaataaga gcttatccca ttagggctat tttacttgcc  240
attttggacc tgggcagtgc tcgccaaaac gcgttagcgt tttgaacgcg ctagcggcgg  300
cccgaagggc gagcgtagcg agtcaaacct cacgtactac gtgtacgctc cggtttttgc  360
gcgctgtccg tgtccaaact gctgcgccaa taacgcctgg tgggataggc tctaaatacg  420
cttcggcgtt cagtaacacg cgttaacgtg ctgaacagcc gggcattttt ttacgctata  480
ccctacataa taaaaccgga gctaccatga ataagaaggt actgacccct tctgccgtga  540
tggcaagtct gttattcggc gcgcacgcgc atgccgccga tgttcctcta actccatctc  600
aatttgctaa agcgaaatca gagaactttg acaagaaagt tattctatct aatctaaata  660
agccgcacgc gttgttatgg ggaccagata atcaaatttg gttaactgag cgagcaacag  720
gtaagattct aagagttaat ccagagtcgg gtagtgtaaa acagttttt caggtaccag  780
agattgtcaa tgatgctgat gggcagaatg gtttattagg ttttgccttc catcctgatt  840
ttaaaaataa tccttatatc tatatttcag gtacatttaa aaatccgaaa tctacagata  900
aagaattacc gaaccaaacg attattcgtc gttataccta taataaatca acagatacgc  960
tcgagaagcc agtcgattta ttagcaggat taccttcatc aaaagaccat cagtcaggtc 1020
gtcttgtcat tgggccagat caaaagattt attatacgat tggtgaccaa gggcgtaacc 1080
agcttgctta tttgttcttg ccaaatcaag cacaacatac gccaactcaa caagaactga 1140
atggtaaaga ctatcacacc tatatgggta agtactacg cttaaatctt gatggaagta 1200
ttccaaagga taatccaagt tttaacgggg tggttagcca tatttataca cttggacatc 1260
gtaatccgca gggcttagca ttcactccaa atggtaaatt attgcagtct gaacaaggcc 1320
caaactctga cgatgaaatt aacctcattg tcaaaggtgg caattatggt tggccgaatg 1380
tagcaggtta taaagatgat agtggctatg cttatgcaaa ttattcagca gcagccaata 1440
agtcaattaa ggatttagct caaaatggag taaaagtagc cgcaggggtc cctgtgacga 1500
aagaatctga atggactggt aaaaactttg tcccaccatt aaaaacttta tataccgttc 1560
aagatacccta caactataac gatccaactt gtggagagat gacctacatt tgctggccaa 1620
cagttgcacc gtcatctgcc tatgtctata agggcggtaa aaaagcaatt actggttggg 1680
aaaatacatt attggttcca tctttaaaac gtggtgtcat tttccgtatt aagttagatc 1740
caacttatag cactacttat gatgacgctg taccgatgtt taagagcaac aaccgttatc 1800
gtgatgtgat tgcaagtcca gatgggaatg tcttatatgt attaactgat actgccggaa 1860
atgtccaaaa agatgatggc tcagtaacaa atacattaga aaacccagga tctctcatta 1920
agttcaccta taaggctaag taatacagtc gcattaaaaa accgatctat aaagatcggt 1980
ttttttagtt ttagaaaaga attcactggc cgtcgtttta caacgtcgtg actgggaaaa 2040
ccctggcgtt acccaactta atcgccttgc agcacatccc ctttcgcca gctggcgtaa 2100
tagcgaagag gcccgcaccg atcgcccttc ccaacagttg cgcagcctga atggcgaatg 2160
gcgcctgatg cggtattttc tccttacgca tctgtgcggt atttcacacc gcatatggtg 2220
cactctcagt acaatctgct ctgatgccgc atagttaagc cagccccgac acccgccaac 2280
acccgctgac gcgccctgac gggcttgtct gctcccggca tccgcttaca gacaagctgt 2340
gaccgtctcc gggagctgca tgtgtcagag gttttcaccg tcatcaccga acgcgcgag 2400
acgaaagggc ctcgtgatac gcctattttt ataggttaat gtcatgataa taatggtttc 2460
ttagacgtca ggtggcactt ttcggggaaa tgtgcgcgga acccctattt gtttattttt 2520
ctaaatacat tcaaatatgt atccgctcat gagacaataa ccctgataaa tgcttcaata 2580
atattgaaaa aggaagagta tgagtattca acatttccgt gtcgccctta ttcccttttt 2640
tgcggcattt tgccttcctg tttttgctca cccagaaacg ctggtgaaag taaaagatgc 2700
tgaagatcag ttgggtgcac gagtgggtta catcgaactg gatctcaaca gcggtaagat 2760
ccttgagagt tttcgccccg aagaacgttt tccaatgatg agcactttta aagttctgct 2820
atgtggcgcg gtattatccc gtattgacgc cgggcaagag caactcggtc gccgcataca 2880
```

Fig. 3b

```
ctattctcag aatgacttgg ttgagtactc accagtcaca gaaaagcatc ttacggatgg 2940
catgacagta agagaattat gcagtgctgc cataaccatg agtgataaca ctgcggccaa 3000
cttacttctg acaacgatcg gaggaccgaa ggagctaacc gctttttttgc acaacatggg 3060
ggatcatgta actcgccttg atcgttggga accggagctg aatgaagcca taccaaacga 3120
cgagcgtgac accacgatgc ctgtagcaat ggcaacaacg ttgcgcaaac tattaactgg 3180
cgaactactt actctagctt cccggcaaca attaatagac tggatggagg cggataaagt 3240
tgcaggacca cttctgcgct cggcccttcc ggctggctgg tttattgctg ataaatctgg 3300
agccggtgag cgtgggtctc gcggtatcat tgcagcactg gggccagatg gtaagccctc 3360
ccgtatcgta gttatctaca cgacggggag tcaggcaact atggatgaac gaaatagaca 3420
gatcgctgag ataggtgcct cactgattaa gcattggtaa ctgtcagacc aagtttactc 3480
atatatactt tagattgatt taaaacttca tttttaattt aaaaggatct aggtgaagat 3540
cctttttgat aatctcatga ccaaaatccc ttaacgtgag ttttcgttcc actgagcgtc 3600
agaccccgta gaaaagatca aaggatcttc ttgagatcct ttttttctgc gcgtaatctg 3660
ctgcttgcaa acaaaaaaac caccgctacc agcggtggtt tgtttgccgg atcaagagct 3720
accaactctt tttccgaagg taactggctt cagcagagcg cagataccaa atactgtcct 3780
tctagtgtag ccgtagttag gccaccactt caagaactct gtagcaccgc ctacatacct 3840
cgctctgcta atcctgttac cagtggctgc tgccagtggc gataagtcgt gtcttaccgg 3900
gttggactca agacgatagt taccggataa ggcgcagcgg tcgggctgaa cggggggttc 3960
gtgcacacag cccagcttgg agcgaacgac ctacaccgaa ctgagatacc tacagcgtga 4020
gctatgagaa agcgccacgc ttcccgaagg gagaaaggcg gacaggtatc cggtaagcgg 4080
cagggtcgga acaggagagc gcacgaggga gcttccaggg ggaaacgcct ggtatcttta 4140
tagtcctgtc gggtttcgcc acctctgact tgagcgtcga ttttgtgat gctcgtcagg 4200
ggggcggagc ctatggaaaa acgccagcaa cgcggccttt ttacggttcc tggccttttg 4260
ctggcctttt gctcacatgt tctttcctgc gttatcccct gattctgtgg ataaccgtat 4320
taccgccttt gagtgagctg ataccgctcg ccgcagccga acgacggggc ccg      4373
```

GENETICALLY ENGINEERED PYRROLOQUINOLINE QUINONE DEPENDENT GLUCOSE DEHYDROGENASE COMPRISING AN AMINO ACID INSERTION

CROSS-REFERENCE TO RELATED APPLICATIONS

This application is a U.S. national counterpart application under 37 C.F.R. § 371(b) of PCT international application ser. no. PCT/EP2005/007844 filed Jul. 19, 2005, which claims priority to European Patent Application No. 04017069.8, filed Jul. 20, 2004.

FIELD OF THE INVENTION

The present invention relates to methods for determining concentrations of sugars, especially glucose in a sample.

The determination of blood glucose concentration is extremely important in clinical diagnosis and in the management of diabetes. Approximately 150 million people worldwide suffer from the chronic disease diabetes mellitus, a figure that may double by 2025 according to the WHO. Although diabetes is readily diagnosed and treated, successful long-term management requires low-cost diagnostic tools that rapidly and accurately report blood glucose concentrations. PQQ-dependent glucose dehydrogenases (EC 1.1.99.17) catalyse a reaction in which glucose is oxidized to gluconolactone. Consequently, this type of enzyme is used in measuring blood sugar. One of these tools is a diagnostic strip based on the soluble glucose dehydrogenase (s-GlucDOR, EC 1.1.99.17), a pyrroloquinoline quinone-containing enzyme originally derived from *Acinetobacter calcoaceticus*.

Quinoproteins use quinone as cofactor to oxidize alcohols, amines and aldoses to their corresponding lactones, aldehydes and aldolic acids (Duine, J. A. Energy generation and the glucose dehydrogenase pathway in *Acinetobacter* in "The Biology of *Acinetobacter*" (1991) 295-312, New York, Plenum Press; Duine, J. A., Eur J Biochem 200 (1991) 271-284; Davidson, V. L., in "Principles and applications of quinoproteins" (1993) the whole book, New York, Marcel Dekker; Anthony, C., Biochem. J. 320 (1996) 697-711; Anthony, C. and Ghosh, M., Current Science 72 (1997) 716-727; Anthony, C., Biochem. Soc. Trans. 26 (1998) 413-417; Anthony, C. and Ghosh, M., Prog. Biophys. Mol. Biol. 69 (1998) 1-21. Among quinoproteins, those containing the noncovalently bound cofactor 2,7,9-tricarboxy-1H-pyrrolo [2,3-f]quinoline-4,5-dione (PQQ) constitute the largest sub-group (Duine 1991, supra). All bacterial quinone glucose dehydrogenases known so far belong to this sub-group with PQQ as cofactor (Anthony and Ghosh 1997 supra, Goodwin, P. M. and Anthony, C., Adv. Microbiol. Physiol. 40 (1998) 1-80; Anthony, C., Adv. in Phot. and Resp. 15 (2004) 203-225).

Two types of PQQ-dependent glucose dehydrogenase (EC 1.1.99.17) have been characterized in bacteria: One is membrane-bound (m-GDH), the other is soluble (s-GDH). Both types do not share any significant sequence homology (Cleton-Jansen, A. M., et al., Mol. Gen. Genet. 217 (1989) 430-436; Cleton-Jansen, A. M., et al., Antonie Van Leeuwenhoek 56 (1989) 73-79; Oubrie, A., et al., Proc. Natl. Acad. Sci. U.S.A 96 (1999) 11787-11791. They are also different regarding both their kinetic as well as their immunological properties (Matsushita, K., et al., Bioscience Biotechnol. & Biochem. 59 (1995) 1548-1555). The m-GDHs are widespread in Gram-negative bacteria, s-GDHs, however, have been found only in the periplasmatic space of *Acinetobacter* strains, like *A. calcoaceticus* (Duine, J. A., 1991a; Cleton-Jansen, A. M. et al., J. Bacteriol. 170 (1988) 2121-2125; Matsushita and Adachi, 1993) and *A. baumannii* (JP 11243949).

Through searching sequence databases, two sequences homologous to the full-length *A. calcoaceticus* s-GDH have been identified in *E. coli* K-12 and *Synechocystis* sp. Additionally, two incomplete sequences homologous to *A. calcoaceticus* s-GDH were also found in the genome of *P. aeruginosa* and *Bordetella pertussis* (Oubrie et al. 1999 a, b, c) and *Enterobacter intermedium* (Kim, C. H. et al., Current Microbiol. 47 (2003) 457-461), respectively. The deduced amino acid sequences of these four uncharacterized proteins are closely related to *A. calcoaceticus* s-GDH with many residues in the putative active site absolutely conserved. These homologous proteins are likely to have a similar structure and to catalyze similar PQQ-dependent reactions (Oubrie et al., 1999 a, b, c; Oubrie A., Biochim. Biophys. Acta 1647 (2003) 143-151; Reddy, S., and Bruice, T. C., J. Am. Chem. Soc. 126 (2004) 2431-2438; Yamada, M. et al., Biochim. Biophys. Acta 1647 (2003) 185-192).

Bacterial s-GDHs and m-GDHs have been found to possess quite different sequences and different substrate specificity. For example, *A. calcoaceticus* contains two different PQQ-dependent glucose dehydrogenases, one m-GDH which is active in vivo, and the other designated s-GDH for which only in vitro activity can be shown. Cleton-Jansen et al., 1988; 1989 a, b cloned the genes coding for the two GDH enzymes and determined the DNA sequences of both of these GDH genes. There is no obvious homology between m-GDH and s-GDH corroborating the fact that m-GDH and s-GDH represent two completely different molecules. (Laurinavicius, V., et al, Biologija (2003) 31-34).

The gene of s-GDH from *A. calcoaceticus* has been cloned in *E. coli*. After being produced in the cell, the s-GDH is translocated through the cytoplasmic membrane into the periplasmic space (Duine, J. A., Energy generation and the glucose dehydrogenase pathway in *Acinetobacter* in "The Biology of *Acinetobacter*" (1991) 295-312, New York, Plenum Press; Matsushita, K. and Adachi, O., Bacterial quinoproteins glucose dehydrogenase and alcohol dehydrogenase in "Principles and applications of Quinoproteins" (1993) 47-63, New York, Marcel Dekker). Like the native s-GDH from *A. calcoaceticus*, recombinant s-GDH expressed in *E. coli* is a homodimer, with one PQQ molecule and three calcium ions per monomer (Dokter, P. et al., Biochem. J. 239 (1986) 163-167; Dokter, P. et al., FEMS Microbiol. Lett. 43 (1987) 195-200; Dokter, P. et al., Biochem. J. 254 (1988) 131-138; Olsthoorn, A. and Duine, J. A., Arch. Biochem. Biophys. 336 (1996) 42-48; Oubrie, A., et al., J. Mol. Biol. 289 (1999) 319-333, Oubrie, A., et al., Proc. Natl. Acad. Sci. U.S.A 96 (1999) 11787-11791, Oubrie, A., et al., Embo J. 18 (1999) 5187-5194). s-GDH oxidizes a wide range of mono- and disaccharides to the corresponding ketones which further hydrolyze to the aldonic acids, and it is also able to donate electrons to PMS (phenazine metosulfate), DCPIP (2,6-dichloro-phenolindophenol), WB (Wurster's blue) and short-chain ubiquinones such as ubiquinone Q1 and ubiquinone Q2 (Matsushita, K., et al., Biochem. 28 (1989) 6276-6280; Matsushita, K., et al., Antonie Van Leeuwenhoek 56 (1989) 63-72), several artificial electron acceptors such as N-methylphenazonium methyl sulfate (Olsthoorn, A. J. and Duine, J. A., Arch. Biochem. Biophys. 336 (1996) 42-48; Olsthoorn, A. J. and Duine, J. A., Biochem. 37 (1998) 13854-13861) and electroconducting polymers (Ye, L., et al., Anal. Chem. 65 (1993) 238-241). In view of s-GDH's high specific activity towards glucose (Olsthoorn, A. J. and Duine, J. A., (1996) supra) and its broad artificial electron acceptor specificity, the enzyme is well suited for analytical applications, particularly for being used in (bio-)sensor or test strips for glucose determination in diagnostic applications (Kaufmann, N. et al., Development and evaluation of a new system for determining glucose from fresh capillary blood and heparinised blood in "Glucotrend" (1997) 1-16, Boehringer Mannheim GmbH; Malinauskas, A.; et al., Sensors and Actuators, B: Chemical B100 (2004) 395-402).

Glucose oxidation can be catalyzed by at least three quite distinct groups of enzymes, i.e., by NAD/P-dependent glucose dehydrogenases, by flavoprotein glucose oxidases or by quinoprotein GDHs (Duine, J. A., Biosens. Bioelectronics 10 (1995) 17-23). A rather slow autooxidation of reduced s-GDH has been observed, demonstrating that oxygen is a very poor electron acceptor for s-GDH (Olsthoorn and Duine, 1996). s-GDH can efficiently donate electrons from the reduced quinone to mediators such as PMS, DCPIP, WB and short-chain ubiquinones such as Q1 and Q2, but it can not efficiently donate electrons directly to oxygen.

Traditional test strips and sensors for monitoring glucose level in blood, serum and urine e. g. from diabetic patients use glucose oxidase. The performance of the enzyme is dependent of the oxygen concentration. Glucose measurements at different altitudes with different oxygen concentrations in the air may lead to false results. The major advantage of PQQ-dependent glucose dehydrogenases is their independence from oxygen. This important feature is e.g., discussed in U.S. Pat. No. 6,103,509, in which some features of membrane-bound GDH have been investigated.

An important contribution to the field has been the use of s-GDH together with appropriate mediators. Assay methods and test strip devices based on s-GDH are disclosed in detail in U.S. Pat. No. 5,484,708. This patent also contains detailed information on the set-up of assays and the production of s-GDH-based test strips for measurement of glucose. The methods described there as well in the cited documents are herewith included by reference.

Other patents or applications relating to the field and comprising specific information on various modes of applications for enzymes with glucose dehydrogenase activity are U.S. Pat. Nos. 5,997,817; 6,057,120; EP 0 620 283; and JP 11-243949-A.

A commercial system which utilizes s-GDH and an indicator that produces a color change when the reaction occurs (Kaufmann et al. 1997 supra) is the Glucotrend® system distributed by Roche Diagnostics GmbH.

Despite the above discussed advantages for use of a PQQ dependent s-GDH, in the determination of glucose also a disadvantage has to be concidered. The enzyme has rather a broad substrate spectrum as compared to m-GDH. That is, s-GDH oxidizes not only glucose but also several other sugars including maltose, galactose, lactose, mannose, xylose and ribose (Dokter et al. 1986 a; Oubrie A., Biochim. Biophys. Acta 1647 (2003) 143-151). The reactivity towards sugars other than glucose may in certain cases impair the accuracy of determining blood glucose levels. In particular patients on peritoneal dialysis, treated with icodextrin (a glucose polymer) may contain in their body fluids, e.g., in blood, high levels of other sugars, especially maltose (Wens, R., et al., Perit. Dial. Int. 18 (1998).603-609).

Therefore clinical samples as e.g. obtained from diabetic patients, especially from patients with renal complications and especially from patients under dialysis may contain significant levels of other sugars, especially maltose. Glucose determinations in samples obtained from such critical patients may be impaired by maltose (Davies, D., Perit. Dial. Int. 14 (1994) 45-50; Frampton, J. E.; and Plosker, G. L., Drugs 63 (2003) 2079-2105).

There are scarce reports in the literature on attempts to produce modified PQQ-dependent s-GDHs with altered substrate specificity. Igarashi, S., et al., Biochem. Biophys. Res. Commun. 264 (1999) 820-824 report that introducing a point mutation at position Glu277 leads to mutants with altered substrate specificity profile.

Sode, EP 1 176 202, reports that certain amino acid substitutions within s-GDH lead to mutant s-GDH with an improved affinity for glucose. In EP 1 167 519 the same author reports on mutant s-GDH with improved stability. Furthermore the same author reports in JP2004173538 on other s-GDH mutants with improved affinty for glucose.

Kratzsch, P. et al., WO 02/34919 report that the specificity of s-GDH for glucose as compared to other sugar substrates, especially as compared to maltose, can be improved by amino acid substitutions in certain positions of s-GDH.

Takeshima, S., et al. (EP 1 367 120) report on mutated s-GDH comprising certain amino acid substitutions or an amino acid insertion between position 427 and 428 as corresponding to the amino acid sequence known from *Acinetobacter calcoaceticus*.

However, whereas quite some improvements have been reported for generating mutants or variants of s-GDH with improved properties further, alternative and/or additional improvements are still required.

A great demand and clinical need therefore exists for additional mutant or variant forms of s-GDH which alone or in combination with already known mutations bring about an improved specificity for glucose as substrate.

It was the task of the present invention to provide new mutants or variants of s-GDH which either alone or in combination with already known mutations lead to a significantly improved substrate specificity for glucose as compared to other selected sugar molecules, e.g., like galactose or maltose.

Surprisingly it has been found that it is possible to significantly improve the substrate specificity of s-GDH for glucose, as compared to other sugars, by making an amino acid insertion between positions 428 and 429 of s-GDH as corresponding to the amino acid sequence known from *Acinetobacter calcoaceticus*, and thus to at least partially overcome the above described problems known in the art.

The substrate specificity for glucose as compared to other selected sugar molecules has been significantly improved by providing the insertion variants of s-GHD according to the present invention and as described herein below and in the appending claims.

Due to the improved substrate specificity of the new forms of s-GDH, significant technical progress for glucose determinations in various fields of applications is possible. The improved s-GDH variants can be used with great advantage for the specific detection or measurement of glucose in biological samples, especially in tests strip devices or in biosensors.

SUMMARY OF THE INVENTION

The present invention relates to a variant of the soluble form of EC 1.1.99.17 also known as PQQ-dependent soluble glucose dehydrogenase (s-GDH) said variant comprising at least one amino acid residue insertion between an amino acid positions corresponding to positions 428 and 429 of the s-GDH wild-type sequence known from *A. calcoaceticus*

(SEQ ID NO: 2) and optionally in addition comprising one or more amino acid substitutions, preferably substitutions at position 348 and 428.

Preferred variants of s-GDH exhibiting improved properties, especially increased specificity for glucose as well as polynucleotide-sequences coding for such variants, an expression vector comprising such polynucleotide sequence, and a host cell comprising said expression vector are also provided.

The invention further relates to the use of a variant according to the present invention in a method for measurement of glucose, especially by a tests strip device or with a biosensor.

The following examples, references, sequence listing and figures are provided to aid the understanding of the present invention, the true scope of which is set forth in the appended claims. It is understood that modifications can be made in the procedures set forth without departing from the spirit of the invention.

DESCRIPTION OF THE INVENTION

FIG. 1: Protein sequences of *A. calcoaceticus* PQQ-dependent s-GDH (top) and *A. baumannii* s-GDH (bottom) aligned according to sequence homology.

FIG. 2: Illustration of pACSGDH vector referred to in Example 1 containing the wild-type or mutated DNA sequences, respectively, of soluble PQQ-dependent glucose dehydrogenase.

FIG. 3: Nucleotide (DNA) sequence of the pACSGDH vector referred to in Example 1 containing the wild-type DNA sequence of soluble PQQ-dependent glucose dehydrogenase.

DETAILED DESCRIPTION OF THE INVENTION

As discussed above, two completely different quinoprotein enzyme types with glucose dehydrogenase activity (membrane bound and soluble) are grouped together under EC 1.1.99.17. These two types appear not be related to each other.

For the purpose of this invention only the soluble form of GDH (s-GDH) is relevant and improved variants thereof are discussed herein below.

In a first embodiment the invention relates to a variant of the soluble form of EC 1.1.99.17 also known as PQQ-dependent soluble glucose dehydrogenase (s-GDH) said variant comprising at least one amino acid residue insertion between the amino acid positions corresponding to positions 428 and 429 of the s-GDH wild-type sequence known from *A. calcoaceticus* (SEQ ID NO: 2) and optionally in addition comprising one or more amino acid substitutions.

Preferably only one amino acid is inserted in between the amino acid positions corresponding to positions 428 and 429 of the s-GDH wild-type sequence known from *A. calcoaceticus* (SEQ ID NO: 2).

It is further preferred that the s-GDH variant comprising an amino acid insertion between the amino acid positions corresponding to positions 428 and 429 of the s-GDH wild-type sequence known from *A. calcoaceticus* (SEQ ID NO: 2) is characterized in that said inserted amino acid is selected from the group consisting of leucin, phenylalanine, methionine and proline. Preferably the inserted amino acid is proline.

It is known in the art that the wild-type DNA-sequence of a soluble PQQ-dependent glucose dehydrogenase can be isolated from strains of *Acinetobacter*. Most preferred is the isolation from *Acinetobacter calcoaceticus*-type strain LMD 79.41. The sequence of this wild-type s-GDH (the mature protein) is given in SEQ ID NO: 2. Other LMD strains of *Acinetobacter* may also be used as source of wild-type s-GDH. Such sequences can be aligned to the sequence obtained from *A. calcoaceticus* and sequence comparisons be made. It also appears feasible to screen DNA-libraries of other bacterial strains, as for example described for *E. coli* K-12 (Oubrie, A., et al., J. Mol. Biol. 289 (1999) 319-333) and to identify sequences related to s-GDH in such genomes. Such sequences and yet unidentified homologous sequences may be used to generate s-GDH variants with improved substrate specificity.

The term "variant" in the sense of the present invention relates to an s-GDH protein which compared to a corresponding wild-type sequence has an amino acid insertion between the amino acid positions corresponding to positions 428 and 429 of the s-GDH wild-type sequence known from *A. calcoaceticus* (SEQ ID NO: 2).

The term "mutant" in the sense of the present invention relates to an s-GDH protein which compared to a corresponding wild-type sequence has at least one amino acid substitution as compared to the s-GDH wild-type sequence known from *A. calcoaceticus* (SEQ ID NO: 2).

The terms "variant", or "mutant" therefore both mutually apply for an s-GDH protein which compared to a corresponding wild-type sequence has an amino acid insertion between the amino acid positions corresponding to positions 428 and 429 of the s-GDH wild-type sequence known from *A. calcoaceticus* (SEQ ID NO: 2) and in addition thereto at least one amino acid substitution.

In a further preferred embodiment the enzymatic or functional properties of an improved variant of s-GDH are compared to the wild-type enzyme or to mutants without an amino acid insertion between position 428 and 429, respectively.

A preferred variant according to the present invention is characterized in that relative to the corresponding wild-type enzyme it has at least a two-fold improved substrate specificity for glucose as compared to at least one other selected sugar substrate.

In order to calculate the substrate specificity or cross-reactivity one easy way is to set the activity measured with glucose as substrate to 100% and to compare the activity measured with the other selected sugar to the glucose value. Sometimes, in order not to be redundant, simply the term specificity is used without making special reference to glucose on the one hand and a selected other sugar substrate on the other hand.

The expert in the field will appreciate that comparison of enzymatic activities is best made at equimolar concentrations of the substrate molecules investigated using well-defined assay conditions. Otherwise corrections for differences in concentrations have to be made.

Standardized and well-defined assay conditions have to be chosen in order to assess (improvements in) substrate specificity. The enzymatic activity of s-GDH for glucose as substrate as well as for other selected sugar substrates is measured as described in Example 7.

Based on these measurements of enzymatic activity for glucose or a selected different sugar, preferably maltose, cross-reactivity (and improvements thereof) is assessed.

The s-GDH (cross-) reactivity for a selected sugar in percent is calculated as

Cross-reactivity [%]=(activity selected sugar/activity glucose)×100%.

(Cross-) reactivity for maltose of wild-type s-GDH according to the above formula has been determined as about 105%. Wild-type s-GDH (cross-) reactivity for galactose has been measured as about 50% (cf. Table 1).

(Improved) specificity is calculated according to the following formula:

$$\text{specificity (improvement)} = \frac{\text{activity glucose mutant}}{\text{activity glucose wild-type}} \times \frac{\text{activity selected sugar wild-type}}{\text{activity selected sugar mutant}}$$

As compared to the wild-type enzyme, a s-GDH form with an at least 10-fold improvement in specificity for glucose versus maltose (maltose/glucose) accordingly with maltose as substrate has at most 10,5% of the activity as measured with glucose as substrate. Or, if, for example a mutant s-GDH has a cross-reactivity for maltose of 20% (determined and calculated as described above), this mutant as compared to the wild-type s-GDH therefore has a 5.25 fold improved substrate specificity (maltose/glucose).

The term "specific activity" for a substrate is well known in the art, it is preferably used to describe the enzymatic activity per amount of protein. Various methods are known to the art to determine specific activity of GDH molecules, using glucose or other sugars as substrates (Igarashi, S., et al., (1999) supra). One of the methods available for such measurement is described in detail in the examples section.

Whereas it is possible, to select many different sugar molecules and to investigate the glucose specificity of s-GDH in comparison to any such selected sugar molecule, it is preferred to select a clinically relevant sugar molecule for such a comparison. Preferred selected sugars are selected from the group consisting of mannose, allose, galactose, xylose, and maltose. Preferably, maltose or galactose are selected and mutant s-GDH is tested for improved substrate specificity for glucose as compared to galactose or maltose. In a further preferred embodiment the selected sugar is maltose.

It has been found that the improvements in glucose specificity of s-GDH variants according to this invention, e.g., for maltose vs. glucose, are quite considerable. It is therefore further preferred that said substrate specificity for glucose as compared to the substrate specificity for at least one of the selected other sugar substrates is improved at least three-fold. Other preferred embodiments comprise s-GDH mutants characterized by an improved substrate specificity for glucose, which is at least 5 times higher or also preferred at least 10 times higher, as compared to the other sugar molecule selected.

Mutations in s-GDH lead in many cases to enzyme variants with dramatically reduced specific activity for the substrate glucose. A more than 10 fold decrease in (absolute or overall) specific activity for the substrate glucose, however, may be critical for routine applications. It is therefore preferred that the s-GDH with improved specificity towards the substrate glucose exhibits at least 10% of the specific activity for glucose as measured with the wild-type enzyme. It is of course more preferred that such mutated enzymes exhibit at least 20% or more preferred at least 30% of the respective glucose activity of wild-type s-GDH.

Further preferred are such mutants for which the maltose specific activity is 10% or less or even only 5% or less of the maltose specific activity as measured for the corresponding wild-type enzyme on test strips or liquid tests, whereas the specific activity for glucose is ≧10% as compared to the specific activity for glucose of the corresponding wild-type enzyme.

It has been found that it is possible to further improve substrate specificity of an s-GDH variant comprising an insertion between position 428 and 429 by further modifying such variant to additionally comprise one or more amino acid substitutions at certain well-defined amino acid positions.

The achievements of the present invention are described in great detail by making reference to amino acid positions known from SEQ ID NO: 2, the wild-type sequence of s-GDH as isolated from *Acinetobacter calcoaceticus*-type strain LMD 79.41. Amino acid positions in different s-GDH isolates corresponding to positions of SEQ ID NO: 2 are easily identified by appropriate sequence comparison.

The multiple alignment and comparison of an s-GDH sequence with the wild-type sequence of SEQ ID NO: 2 is performed with the PileUp program of GCG Package Version 10.2 (Genetics Computer Group, Inc.). PileUp creates a multiple sequence alignment using a simplification of the progressive alignment method of Feng, D. F. and Doolittle, R. F., J. Mol. Evol. 25 (1987) 351-360, and the scoring matrixes for identical, similar, or different amino acid residues are defined accordingly. This process begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments that include increasingly dissimilar sequences and clusters, until all sequences have been included in the final pairwise alignment. This way positions in other, homologous s-GDH molecules be easily identified as corresponding to the positions given for *A. calcoaceticus* s-GDH in SEQ ID NO: 1 and 2, respectively. This is why the amino acid positions given herein shall be understood as amino acid positions of SEQ ID NO: 2 or as the positions corresponding thereto in another, homologous s-GDH molecule.

Mutants of s-GDH comprising an amino acid substitution at the position corresponding to position 348 in combination with an amino acid insertion between position 428 and 429 of s-GDH have been found to exhibit a striking positive effect with respect to specificity for glucose. As demonstrated in table 1, a variety of s-GDH variants with improved specificity for glucose has been identified and generated. Improvement of glucose specificity for a variant s-GDH is seen as long as the amino acid in position threonine 348 is substituted with an appropriate other amino acid and an appropriate amino acid is inserted between position 428 and 429. A very preferred embodiment of the present invention therefore relates to a variant protein of PQQ-dependent s-GDH comprising an insertion between the amino acids 428 and 429 of the s-GDH wild-type sequence known from *A. calcoaceticus* (SEQ ID NO: 2) and in addition comprising an amino acid residue substitution at the amino acid position corresponding to position 348.

It has also been found, that further substitutions at amino acid an amino acid position corresponding to positions 169, 171, 245, 341, 349, and/or 428 of SEQ ID NO: 2 are advantageous in efforts of further improving the specificity for glucose of an s-GDH variant comprising an insertion between the amino acids 428 and 429 and an amino acid residue substitution at position 348.

Neither the threonine residue at position 348 nor the insertion of an amino acid between position 428 and 429 of s-GDH as isolated from *Acinetobacter calcoaceticus*-type strain LMD 79.41 are known from the art to contribute to the substrate binding of s-GDH (Oubrie, A., et al., Embo J. 18 (1999) 5187-5194; Oubrie, A. and Dijkstra, B. W., Protein Sci. 9 (2000) 1265-1273). No chemical or physical explanation is at hand, why especially these two modifications of s-GDH improve the substrate specificity for glucose as compared to other sugar molecules of interest, especially as compared to maltose.

In a further preferred embodiment the variant s-GDH is characterized in that the amino acid residue threonine at position 348 is substituted with an amino acid residue selected from the group consisting of alanine, glycine, and serine. In a more preferred embodiment glycine is used to substitute for threonine at position 348. The terminology T348G is known to the skilled artisan and indicates that threonine at position 348 is replaced by glycine.

An additional preferred embodiment is a variant of the soluble form of EC 1.1.99.17 also known as PQQ-dependent soluble glucose dehydrogenase (s-GDH) said variant comprising at least one amino acid residue insertion between an amino acid positions corresponding to positions 428 and 429 of the s-GDH wild-type sequence known from *A. calcoaceticus* (SEQ ID NO: 2) and at least one amino acid residue substitution at an amino acid position corresponding to position 428. Preferably the substitution of the asparagine at position 428 is by leucine, proline and valine. More preferred the substitution in position 428 is by proline.

One group of preferred s-GDH variants according to this invention comprises a substitution of the amino acid residue at position 348, and/or an amino acid substitution at position 428, and an amino acid insertion between position 428 and 429. These variants may optionally further be modified to comprise one or more amino acid substitutions at amino acid positions corresponding to positions 169, 171, 245, 341, and/or 349 of the s-GDH wild-type sequence known from *A. calcoaceticus* (SEQ ID NO: 2).

In case the amino acid corresponding to position 169 of the s-GDH wild-type sequence known from *A. calcoaceticus* (SEQ ID NO: 2) is substituted in a variant of the present invention, it is preferred that the naturally occurring amino acid leucine is substituted by phenylalanine, tyrosine or tryptophane. More preferred the substitution in position 169 is by phenylalanine.

In case the amino acid corresponding to position 171 of the s-GDH wild-type sequence known from *A. calcoaceticus* (SEQ ID NO: 2) is substituted in a variant of the present invention, it is preferred that the naturally occurring amino acid tyrosine is substituted by an amino acid selected from the group consisting of from the group consisting of alanine, methionine, glycine. More preferred the substitution in position 171 is by glycine.

In case the amino acid corresponding to position 245 of the s-GDH wild-type sequence known from *A. calcoaceticus* (SEQ ID NO: 2) is substituted in a variant of the present invention, it is preferred that the naturally occurring amino acid glutamic acid is substituted by aspartic acid, asparagine or glutamine. More preferred the substitution in position 245 is by aspartic acid.

In case the amino acid corresponding to position 341 of the s-GDH wild-type sequence known from *A. calcoaceticus* (SEQ ID NO: 2) is substituted in a variant of the present invention, it is preferred that the naturally occurring amino acid methionine is substituted by, valine, alanine, leucine or isoleucine. More preferred the substitution in position 341 is by valine.

In case the amino acid corresponding to position 349 of the s-GDH wild-type sequence known from *A. calcoaceticus* (SEQ ID NO: 2) is substituted in a variant of the present invention, it is preferred that the naturally occurring amino acid valine is substituted by alanine, glycine. More preferred the substitution in position 349 is by alanine.

As described in WO 02/34919, a substitution of the amino acid in position 348 of the s-GDH sequence corresponding to the wild-type sequence isolated from *A. calcoaceticus*, can be used to significantly improve the glucose specificity of s-GDH. The skilled artisan will find in WO 02/34919 other appropriate positions which may be substituted and combined with the insertion according to the present invention.

In a further preferred embodiment the s-GDH variant according to the present invention in addition to the insertion between amino acid residues 428 and 429 comprises at least two amino acid substitutions selected from the group consisting of positions 171, 245, 341, 348 and 349 as corresponding to amino acid positions of the s-GDH wild-type sequence known from *A. calcoaceticus* (SEQ ID NO: 2).

In yet a further preferred embodiment the s-GDH variant according to the present invention in addition to the insertion between amino acid residues 428 and 429 comprises at least three amino acid substitutions selected from the group consisting of positions 171, 245, 341, 348 and 349 as corresponding to amino acid positions of the s-GDH wild-type sequence known from *A. calcoaceticus* (SEQ ID NO: 2).

As the skilled artisan will appreciate, it is possible to undertake amino acid substitutions, e.g. silent mutations, which do not influence the properties of s-GDH to a significant extend. The variant according to the present invention will, however, have no more than 45 amino acid exchanges as compared to SEQ ID NO: 2. Preferably the variant will comprise 20 or less amino acid substitutions, more preferred, only 10 amino acid substitutions or less substitutions will be present.

s-GDH variants according to the present invention are given in the Examples section. These variants also represent preferred embodiments of the invention. The variants with least glucose interference found so far comprise the insertion between amino acids 428 and 429, preferably by proline, and the mutations Y171G, E245D, M341V and T348G or the mutations L169F, Y171G, E245D, M341V and T348G, respectively. These two variants also are further preferred embodiments of the present invention.

Amino acid sequence analysis revealed that the sequence motives found in wild-type s-GDH from *A. calcoaceticus* on the one hand and *A. baumannii* on the other hand appear to be very conservative around the positions of major relevance to improve the specificity for glucose as identified in the present invention, i.e., the insertion site around position 428 and 429 as corresponding to wild-type s-GDH from *A. calcoaceticus*.

A variant of PQQ-dependent s-GDH, comprising the amino acid sequence of AGNXaaVQK (SEQ ID NO: 2), represents a preferred embodiment of the present invention. SEQ ID NO: 2 corresponds to position 426-431 of *A. calcoaceticus* wild-type s-GDH or to position 427-432 of *A. baumannii* wild-type s-GDH but comprising the insertion of one amino acid (Xaa) between positions 428 and 429 (*A. calcoaceticus*), or between 429 and 430 (*A. baumannii*), respectively.

In a preferred embodiment the present invention relates to a variant s-GDH comprising the sequence G-N-Xaa-V-Q-K-D (SEQ ID NO: 11). Preferably the s-GDH variant comprising SEQ ID NO: 11 is further characterized in that said inserted amino acid Xaa is selected from the group consisting of leucine, proline phenylalanine and methionine, more preferred Xaa is a proline residue.

As explained further above the amino acid asparagine at position 428 of wild-type s-GDH may be subject to an amino acid substitution. In this case SEQ ID NO: 11 will comprise the substituted amino acid instead of P428.

Numerous possibilities are known in the art to produce mutant proteins. Based on the important findings of the present invention disclosing the critical importance an amino acid insertion between position 428 and 429, the skilled artisan now can easily produce further appropriate variants of s-GDH. Such variants for example can be obtained by the methods known as random mutagenesis (Leung, D. W., et al., Technique 1 (1989) 11-15) and/or directed mutagenesis (Hill, D. E., et al., Methods Enzymol. 155 (1987) 558-568). An alternative method to produce a protein with the desired properties is to provide chimaeric constructs, which contain sequence elements from at least two different sources or to completely synthesize an appropriate s-GDH gene. Such procedures known in the art may be used in combination with the information disclosed in the present invention to provide mutants or variants of s-GDH comprising e.g. additional amino acid substitutions in combination with the disclosed insertion between position 428 and 429 of SEQ ID NO: 2.

A s-GDH variant according to the present invention can e.g., be produced by starting from a s-GDH gene as isolated from *Acinetobacter calcoaceticus*-type strain LMD 79.41 as well as by starting from a homologous sequence. In the context of this application the term "homologous" is meant to comprise an s-GDH amino acid sequence with at least 90% identity as compared to SEQ ID NO: 2. With other words, after appropriate alignment using the PileUp program, at least 90% of the amino acids of such homologous s-GDH are identical to the amino acids described in SEQ ID NO: 2.

It will be understood that variations of DNA and amino acid sequences naturally exist, or may be intentionally introduced using methods known in the art. These variations may result in up to 10% amino acid differences in the overall sequence, due to deletions, substitutions, insertions, inversions or additions of one or more amino acid residues in said sequence as compared to SEQ ID NO: 2. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the afore mentioned polypeptides, as well as precursors of the aforementioned polypeptides, for example, precursors having N-terminal substitution such as methionine, N-formylmethionine used as leader sequences. Such variations may be made without necessarily departing from the scope and the spirit of the present invention.

According to procedures known in the state of the art or according to the procedures given in the examples section, it is possible to obtain polynucleotide sequences coding for any of the s-GDH mutants as discussed above. The invention therefore comprises also isolated polynucleotide sequences encoding s-GDH mutant proteins as described above.

The present invention further includes an expression vector comprising a nucleic acid sequence according to the present invention operably linked a promoter sequence capable of directing its expression in a host cell.

The present invention further includes an expression vector comprising a nucleic acid sequence according to the present invention operably linked to a promoter sequence capable of directing its expression in a host cell. Preferred vectors are plasmids such as pACSGDH shown in FIGS. 2 and 3.

Expression vectors useful in the present invention typically contain an origin of replication, an antibiotica resitance for selection, a promoter for expression and the whole or part of the s-GDH gene variant. The expression vectors may also include other DNA sequences known in the art, like signal sequences (for a better folding, transportation into the periplasma or secretion), inducers for a better modulation of the expression, or cleavage sites for cloning.

The characteristics of the selected expression vector must be compatible to the host cell, which is to be employed. For example, when cloning in an *E. coli* cell system, the expression vector should contain promoters isolated from the genome of *E. coli* cells (e.g., lac, or trp). Suitable origins of replication like the ColE1 plasmid replication origin can be used. Suitable promoters include, for example, lac and trp. It is also preferred that the expression vector includes a sequence coding for a selection marker like an antibiotic resistance gene. As selectable markers, ampicillin resistance, or canamycin resistance may be conveniently employed. All of these materials are known in the art and are commercially available.

Suitable expression vectors containing the desired coding and control sequences may be constructed using standard recombinant DNA techniques known in the art, many of which are described in Sambrook et al., in "Molecular Cloning: A Laboratory Manual" (1989) Cold Spring Harbor, N.Y., Cold Spring Harbour Laboratory Press.

The present invention additionally relates to host cells containing an expression vector which comprises a DNA sequence coding for all or part of the mutant s-GDH. The host cells preferably contain an expression vector that comprises all or part of one of the DNA sequences having one or more mutations shown in the examples 2-8. Suitable host cells include, for example, *E. coli* HB101 (ATCC 33694) available from Pomega (2800 Woods Hollow Road, Madison, Wis., USA), XL1-Blue MRF' available from Stratagene ( 11011 North Torrey Pine Road, La Jolla, Calif., USA) and the like.

Expression vectors may be introduced into host cells by various methods known in the art. For example, transformation of host cells with expression vectors can be carried out by polyethylene glycol mediated protoplast transformation method (Sambrook et al. 1989 supra). However, other methods for introducing expression vectors into host cells, for example, electroporation, biolistic injection, or protoplast fusion, can also be employed.

Once an expression vector containing an s-GDH variant has been introduced into an appropriate host cell, the host cell may be cultured under conditions permitting expression of the desired s-GDH variants. Host cells containing the desired expression vector with the DNA sequence coding for all or part of the mutant s-GDH can be easily identified by i.e. anitbiotica selection. The expression of the s-GDH variants can be identified by different methods like measuring production of s-GDH mRNA transcripts, detection of the gene product immunologically or detection of the enzymatic activity of the gene product. Preferably an enyzmatic assay is applied.

The present invention also teaches the generation and screening of s-GDH variants. Random mutagenesis and saturation mutagenesis is performed as known in the art. Variants are screened for substrate specificity (activity with glucose compared to maltose) and the KM value for glucose. The assay conditions chosen are adapted to ensure that the expected small enhancements brought about e.g., by a single amino acid substitution, can be measured. One mode of selection or screening of appropriate mutants is given in Example 3. Any change or improvement as compared over the wild-type enzyme this way can be clearly detected.

It should, of course, be understood that not all expression vectors and DNA regulatory sequences would function equally well to express the DNA sequences of the present invention. Neither will all host cells function equally well with the same expression system. However, one of ordinary skill in the art will make an appropriate selection among the expression vectors, DNA regulatory sequences, and host cells using the guidance provided herein without undue experimentation.

The invention also relates to a process for producing s-GDH variants of the current invention comprising culturing a host cell of the invention under conditions suitable for production of the mutant s-GDH of the invention. For bacterial host cells, typical culture conditions are liquid medium containing carbon and nitrogen sources, the appropriate antibiotic and induction agent (depending on the used expression vector). Typical appropriate antibiotics include ampicillin, canamycin, chloroamphenicol, tetracyclin and the like. Typical induction agents include IPTG, glucose, lactose and the like.

It is preferred that the polypeptides of the present invention are obtained by production in host cells expressing a DNA sequence coding the mutant s-GDH. The polypeptides of the present invention may also be obtained by in vitro translation of the mRNA encoded by a DNA sequence coding for the mutant s-GDH. For example, the DNA sequences may be synthesized as described above and inserted into a suitable expression vector, which in turn may be used in an in vitro transcription/translation system.

An expression vector comprising an isolated polynucleotide as defined and described above operably linked to a promoter sequence capable of promoting its expression in a cell-free peptide synthesis system represents another preferred embodiment of the present invention.

The polypeptides produced e.g. by procedures as describe above, may then be isolated and purified using various routine protein purification techniques. For example, chromatographic procedures such as ion exchange chromatography, gel filtration chromatography and affinity chromatography may be employed.

One of the major applications of the improved s-GDH variants of this invention is for the use in test strips to monitor blood-glucose level in diabetic patients. The insensitivity of PQQ-dependent glucose dehydrogenase towards oxygen is, as discussed above, a big advantage over glucose oxidase. More important, since the s-GDH variants have improved specificity towards glucose and significantly decreased enzymatic activity towards other sugars, the interference due maltose, galactose, and/or other related sugars which may be present in a sample to be analyzed, is significantly reduced. Of course many kinds of samples may be investigated. Bodily fluids like serum, plasma, intestinal fluid or urine are preferred sources for such samples.

The invention also comprises a method of detecting, determining or measuring glucose in a sample using a s-GDH mutant according to the present invention. It is especially preferred that the improved method for detection of glucose in a sample is characterized in that said detection, determination or measurement of glucose is performed using a sensor or test strip device.

Also within the scope of the present invention is a device for the detection or measurement of glucose in a sample comprising a s-GDH mutant according to this invention as well as other reagents required for said measurement.

The s-GDH variants with improved substrate specificity of this invention can also be used to great advantage in biosensors (D' Costa, E. J., et al., Biosensors 2 (1986) 71-87; Laurinavicius, V., et al., Analytical Letters 32 (1999) 299-316; Laurinavicius, V., et al., Monatshefte fuer Chemie 130 (1999) 1269-1281; Malinauskas, A. et al., Sensors and Actuators, B: Chemical 100 (2004) 395-402) for online monitoring of glucose in a sample or a reactor. For this purpose, the s-GDH variants can, for example, be used to coat an oxygen-insensitive glassy electrode with an osmium complex containing a redox conductive epoxy network (Ye et al., 1993 supra) for more accurate determination of the glucose concentration.

There are also other possible applications of the s-GDH variants with the improved substrate specificity according to this invention. For example, these s-GDH variants may be used in an aldonic acid production process. Wild-type s-GDH has a high turnover in substrate oxidation producing gluconic and other aldonic acids. By using the s-GDH variants, which are more specific for glucose, the production of gluconic acid would result in much less byproducts. With other s-GDH variants of different substrate specificity, it is possible to produce different aldonic acids as required.

In the following examples, all reagents, restriction enzymes, and other materials were obtained from Roche Diagnostics Germany, unless other commercial sources are specified, and used according to the instructions given by the suppliers. Operations and methods employed for the purification, characterization and cloning of DNA are well known in the art (Ausubel, F., et al., in "Current protocols in molecular biology" (1994) Wiley Verlag) and can be adapted as required by the skilled artisan.

The following examples further illustrate the present invention. These examples are not intended to limit the scope of the present invention, but provide further understanding of the invention.

EXAMPLE 1

Cloning and Expression of the Wild-type *A. alcoaceticus* Soluble PQQ Dependent Glucose Dehydrogenase in *E. coli*

The s-GDH gene was isolated from *Acinetobacter calcoaceticus* strain LMD 79.41 according to standard procedures. The wild-type s-GDH gene was subcloned into a plasmid containing the mgl promoter for adjustable expression (cf. Patent application WO 88/09373). The new construct was called pACSGDH (see FIGS. 2 and 3). The recombinant plasmids were introduced into a host organism selected from the *E. coli* group. These organisms were then cultivated under appropriate conditions and colonies showing s-GDH activity selected.

The plasmid pACSGDH was isolated from a 200 ml overnight culture of the done mentioned above using the QIAGEN Plasmid Maxi Kit (Qiagen) according to the manufacturers' protocol. The plasmid was resuspended in 1 ml bidest water. The concentration of the plasmid was determined using a Beckman DU 7400 Photometer.

The yield was 600 µg. Then the quality of the plasmid was determined by agarose gel electrophoresis.

EXAMPLE 2

Generating Mutant T348G

As an important starting template for the generation of insertion variants a mutant s-GDH with the mutation T348G was manufactured. This mutant of s-GDH was chosen because it is known to have reduced activity to maltose compared to glucose (see WO 02/34919).

The QuickChange Site-Directed Mutagenesis Kit (Stratagene, Cat. 200518) was used to substitute the threonine at position 348 by a glycine. The appropoiate primers were designed.

The 5'- and the 3'-primer used for mutagenesis were complementary to each other and contained the modified codon for the exchange from threonine to glycine (ACA to GGG) in a central position. These nucleotides were flanked by 12 to 16 nucleotides at each end. The sequences of the nucleotides were identical to the sense and anti-sense DNA-strand flanking the codon for the amino acid exchange. Instead of the codon ACA=threonine for the sense and TGT for the anti-sense strand, the primers contained GGG=glycine for the sense and CCC for the anti-sense strand (see SEQ ID NOs: 3 and 4).

The PCR-reaction and the DpnI digestion were performed according to the manual. After that, 1 µl of sample was used for the electroporation of XL-MRF'- cells. Electroporation was achieved with 2.5 KV in 0.2 cm cuvettes using a BioRad E. coli Pulser (BioRad). After growth in 1 ml LB at 37° C. for one hour, bacteria were plated on LB-Ampicillin agar plates (100 µg / ml Ampicillin) and grown over night at 37° C. The mutated s-GDH clones were examined using the following screening method.

EXAMPLE 3

Screening

The mutant colonies on the agar plates described above where picked into microtiter plates (MTPs) containing 200 µl LB-Ampicillin-media/well and incubated over night at 37° C. These plates are called master plates.

From each master plate, 5 µl sample/well was transferred to an MTP containing 5 µl per/well of B (B=Bacterial Protein Extraction Reagent; Pierce No. 78248) for cell disruption and 240 µl of 0.0556 mM pyrollo-quinoline quinone (PQQ); 50 mM Hepes; 15 mM $CaCl_2$ pH 7.0/well for activation of s-GDH were added. To complete the formation of the holoenzyme, the MTP was incubated at 25° C. for 2 hours and at 10° C. over night. This plate is called working plate.

From the working plate 3×10 µl sample/hole were transferred to three empty MTPs. After that, one was tested with glucose at standard concentration, the second one with a reduced glucose concentration (1.9 mM instead of 30 mM) and the third with maltose or another selected sugar molecule as a substrate. All selected other sugar molecules were used in equimolar standard concentration, i.e. at 30 mM. For all assays 90 µl of mediator solution (see Example 7) already containing the sugar to be analyzed was applied.

The dE/min was calculated and the value using 30 mM glucose as substrate was set to 100% activity. The value obtained with the other sugar was compared to the glucose value and calculated in percent activity ((e.g. for maltose as: dE/min maltose/dE glucose)*100). This is equivalent to the cross-reactivity of the (variant) enzyme.

The value obtained with the 1.9 mM glucose was compared to the 30 mM glucose value and calculated in percent activity ((dE/min 1.9 mM glucose/30 mM glucose)*100). This gives a %-value which is an indirect indicator of the KM value for the variant analyzed. According to this calculation a higher %-value indicates a lower (=better) KM value.

The following mutant has been identified:

| Enzyme | M/G (30 mM sugar in %) | Activity 1.9/30 mM glucose in % | Amino acid exchanges |
|---|---|---|---|
| WT | 105 | 70% | — |
| mutant | 25-30% | 21% | T348G |

EXAMPLE 4

Sequencing of Mutant s-GDH Gene from Site Directed Mutagenesis

The plasmid containing the gene for mutant s-GDH T348G, which mutant has a 25-30% maltose/glucose cross-reactivity was isolated (High Pure Plasmid Isolation Kit, Roche Diagnostics GmbH, No. 1754785) and sequenced using an ABI Prism Dye Terminator Sequencing Kit and ABI 3/73 and 3/77 sequencer (Amersham Pharmacia Biotech).

Following primers were used:

```
Sense strand:
                                    (= SEQ ID NO:.5)
    GDH 1: 5'-TTA ACG TGC TGA ACA GCC GG-3'

(= SEQ ID NO:6)
    GDH 2: 5'-ATA TGG GTA AAG TAC TAC GC-3'
```

Result:

Desired mutation on DNA and amino acid level has been achieved, resulting in change from T to G at position 348 (mature enzyme). No additional mutation on gene has been found.

EXAMPLE 5

Generating Insertion Variants on Basis of Mutant T348G

Insertion variants were created by using the QuickChange Site-Directed Mutagenesis Kit (Stratagene, Cat. 200518). The appropriate primers for the insertion between amino acid positions 428 and 429 (see sequence: ID NO: 2) were designed and a PCR with a mutant of s-GDH (mutant T348G, see Example 4) performed according to the manufacturers description.

For the primers the respective codon at the insertion position was synthetisized at random to get all possible 20 amino acids exchanges. These codon nucleotides were flanked by 11 to 13 nucleotides at each end.

```
sense strand:
                                    (= SEQ ID NO:7)
    in429X_F: 5'-CTGCCGGAAATNNNGTCCAAAAAGATG-3' anti-sense strand:
                                    (= SEQ ID NO:8)
    in429X_R  5'-CATCTTTTTGGACNNNATTTCCGGCAG-3'
```

The PCR-reaction and the DpnI digestion were performed according to the manual. After that, 1 µl of each reaction was used for the electroporation of XL1F- cells as described above. After growth in 1 ml LB at 37° C. for one hour, bacteria were plated on LB-Ampicillin agar plates (100 µg / ml Ampicillin) and grown over night at 37° C. The mutated s-GDH clones were subjected to the described screening procedure. To ensure statistically that variants with the 20 possible amino acid insertions were screened, 200 clones were tested. Clones with altered substrate specificity were subjected to plasmid isolation and sequenzed as described above.

Results:

TABLE 1

| Enzyme | M/G (30 mM sugar in %) | Activity 1.9/30 mM glucose in % | Amino acid exchanges |
|---|---|---|---|
| WT | 105 | 70% | — |
| MutantA | 25% | 21% | T348G |
| A/2 | 36% | 33% | T348G + ins429G |
| A/3 | 34% | 21% | T348G + ins429K |
| A/4 | 19% | 23% | T348G + ins429F |
| A/5 | 26% | 24% | T348G + ins429V |
| A/6 | 22% | 24% | T348G + ins429L |
| A/7 | 16% | 17% | T348G + ins429M |
| A/8 | 18% | 31% | T348G + ins429P |

EXAMPLE 6

Generating Further Insertion Mutants with High Substrate Specificity for Glucose as Compared to Maltose In WO 02/34919 several amino acid exchanges at different positions of s-GDH have been identified to enhance the substrate specificity for glucose as compared to e.g., maltose. Combinations of the amino acid exchange T348G with amino acid 10 substitutions at other positions for example at positions 169, 171, 245, 341, and/or 349 enhanced the substrate specificity furthermore. Two of the mutants described there with substrate specificities for maltose/glucose of 3,5 and 7%, respectively, were selected to receive the insertion (in this case proline) according to the present invention between positions 428 and 429. The insertion was accomplished by using the primers of SEQ ID NOs: 9 and 10.

```
SEQ ID NO:9 insP429_F:
5'-GATACTGCCGGAAATCCAGTCCAAAAAG-3'

SEQ ID NO:10 insP429_R:
5'-CTTTTTGGACTGGTCCTCCGGCAGTATC-3'
```

The plasmid DNA isolation of the templates, site-directed mutagenesis PCR, electroporation, screening, DNA sequencing of selected mutants was done as described above.

Results:

| Enzyme | M/G (30 mM sugar) in % | Activity 1.9/30 mM glucose in % | Amino acid exchanges |
|---|---|---|---|
| WT | 105 | 70% | — |
| Template C/0 | 7% | 9% | Y171G + E245D + M341V + T348G |
| Insertion mutant C/1 | 4% | 14% | Y171G + E245D + M341V + T348G + ins429P |
| Template D/0 | 3.5% | 10% | L169F + Y171G + E245D + M341V + T348G |
| Insertion mutant D/1 | 2% | 9% | L169F + Y171G + E245D + M341V + T348G + ins429P |

It can be clearly seen from the above table that the substrate specificity maltose/glucose has changed dramatically. The maltose conversion has been found to be diminished from 105% to 2-4% as compared to the maltose/glucose conversion of the wild-type s-GDH. Mutants C/1 and D/1 were examined in detail.

EXAMPLE 7

Purification and Analysis of Enzymatic Activity for Wild-type or Variant s-GDH, Respectively The grown cells (LB-Amp. 37° C.) were harvested and resuspended in potassium phosphate buffer pH 7.0. Cell disruption was performed by French Press passage (700-900 bar). After centrifugation the supernatant was applied to a S-Sepharose (AmershamBiosciences) column equilibrated with 10 mM potassium phosphate buffer pH 7.0. After washing, the s-GDH was eluted using a salt gradient 0-1 M NaCl. The fractions showing s-GDH activity were pooled, dialysed against potassium phosphate buffer pH 7.0 and re-chromatographied on re-equilibrated S-sepharose column. The active fractions were pooled and subjected to a gel filtration using a Superdex® 200 column (Amersham Biosciences). The active fractions were pooled and stored at −20° C.

Enzyme Assay and Protein Determination of Purified Wild-type and Variant s-GDH, Respectively:

Protein determination was performed using the Protein Assay Reagent no. 23225 from Pierce (calibration curve with BSA, 30 Min. 37° C.).

The GDH samples were diluted to 1 mg protein/ml with 0.0556 mM pyrollo-quinoline quinone (PQQ); 50 mM Hepes; 15 mM CaCl2 pH 7.0 and incubated at 25° C. for 30 minutes for reconstitution or activation.

After activation, samples were diluted with 50 mM Hepes; 15 mM CaCl2 pH 7.0 to approximately 0,02 U/ml, and 50 µl of each diluted sample was added to 1000 µl of a 0.2 M citrate buffer solution (pH 5.8; at 25° C.) containing 0.315 mg (4-(dimethylphosphinylmethyl)-2-methyl-pyrazolo-[1.5a]-imidazol-3-yl)-(4-nitrosophenyl)-amine (see patent U.S. Pat. No. 5,484,708)/ml as a mediator and 30 mM sugar).

Extinction at 620 nm is monitored during the first 5 minutes at 25° C.

One Unit enzyme activity corresponds the conversion of 1 mMol mediator/min under the above assay conditions Calculation: Activity=(total volume*dE/min [U/ml]):
($\epsilon$*sample volume*1) ($\epsilon$=coefficient of extinction; $\epsilon_{620\,nm}$=30[1*mmol$^{-1}$*cm$^{-1}$]).

The assay was performed with glucose and maltose (Merck, Germany), respectively.

Results:

| Enzyme | M/G (30 mM sugar in %) | U/mg Protein. | Amino acid exchanges |
|---|---|---|---|
| WT | 105 | 800 | — |
| C/1 | 4% | 106 | Y171G + E245D + M341V + T348G + ins429P |
| D/1 | 1.5% | 109 | L169F + Y171G + E245D + M341V + T348G + ins429P |

It is obvious from the above table that the novel variants C/1 and D/1, comprising an insertion between positions 428 and 429 of s-GDH represent further improvements with respect to the maltose/glucose cross-reactivity. Despite of the various amino acid substitutions and despite of the insertion, the enzymatic activity for glucose per mg/protein is still more than 10% of the corresponding wild-type enzymatic activity.

EXAMPLE 8

Determination of Glucose in the Presence or Absence of Maltose

The wild-type s-GDH and variants C/1 and D/1 of s-GDH, respectively, can be applied for glucose determination in the presence or absence of maltose. The reference sample contains 50 mg glucose/dl. The "test"-sample containes 50 mg glucose/dl and 100 or 200 mg/dl maltose, respectively. The same amounts of GDH activity (U/ml; see enzyme assay above) are used for each assay.

In a cuvette are mixed:
1 ml 0.315 mg (4-(dimethylphosphinylmethyl)-2-methyl-pyrazolo-[1.5a]-imidazol-3-yl)-(4-nitrosophenyl)-amine ml/0.2 M citrate pH 5.8
0.033 ml reference or test sample The assay is started by adding of 0.050 ml s-GDH (which is an excess of s-GDH for conversion of glucose) to the cuevette. The change of absorption at 620 nm is monitored. After 2-5 minutes constant values are observed and the dE/5 min is calculated. The value obtained measuring the reference sample with wild-type s-GDH is set to 100%. The other values are compared to this reference value and calculated in %.

Results:

Clearly less maltose interference is detected in the test samples when using the novel variants. It is obvious that the concentration of s-GDH in order to best discriminate glucose from maltose in a sample can be further optimized. Too much enzyme would increase the maltose conversion, too little enzyme would not convert all glucose and thus no endpoint of the absorption would be reached.

List of References

Anthony C., Biochem. J. 320 (1996) 697-711
Anthony, C. and Ghosh, M., Current Science 72 (1997) 716-727
Anthony, C. and Ghosh, M., Prog. Biophys. Mol. Biol. 69 (1998) 1-21
Anthony, C., Biochem. Soc. Trans. 26 (1998) 413-417
Anthony, C., Adv. in Phot. and Resp. 15 (2004) 203-225
Ausubel, F., et al., in "Current protocols in molcular biology" (1994), Wiley Verlag
Cleton-Jansen, A. M., et al., Antonie Van Leeuwenhoek 56 (1989) 73-79
Cleton-Jansen, A. M., et al., J. Bacteriol. 170 (1988) 2121-2125
Cleton-Jansen, A. M., et al., Mol. Gen. Genet 217 (1989) 430-436
Davidson, V. L. in "Principles and applications of quinoproteins" (1993) the whole book, New York, Marcel Dekker
Davies, D., Perit. Dial. Int. 14 (1994) 45-50
D'Costa, E. J., et al., Biosensors 2 (1986) 71-87
Dokter, P., et al., FEMS Microbiology Letters 43 (1987) 195-200
Dokter, P., et al., Biochem J. 239 (1986) 163-167
Dokter, P., et al., Biochem J. 254 (1988) 131-138
Duine, J. A. Energy generation and the glucose dehydrogenase pathway in *Acinetobacter* in "The Biology of *Acinetobacter* " (1991) 295-312, New York, Plenum Press
Duine, J. A., Biosens. Bioelectronics 10 (1995) 17-23
Duine, J. A., Eur. J. Biochem. 200 (1991) 271-284
EP 0 620 283
EP 1 167 519
EP 1 176 202
EP 1 367 120
Feng, D. F. and Doolittle, R. F., J. Mol. Evol. 25 (1987) 351-360
Frampton, J. E. and Plosker, G. L., Drugs 63 (2003) 2079-2105
Goodwin, P. M. and Anthony, C., Adv. Microbiol. Physiol. 40 (1998) 1-80
Hill, D. E., et al., Methods Enzymol. 155 (1987) 558-568
Igarashi, S., et al., Biochem. Biophys. Res. Commun. 264 (1999) 820-824
JP 11243949
JP 2004173538
Kaufmann, N., et al. Development and evaluation of a new system for determining glucose from fresh capillary blood and heparinised venous blood in "Glucotrend" (1997) 1-16, Mannheim, Boehringer Mannheim GmbH
Kim, C. H. et al., Current Microbiology 47 (2003) 457-461
Laurinavicius, V., et al., Analytical Letters 32 (1999) 299-316
Laurinavicius, V., et al., Monatshefte fuer Chemie 130 (1999) 1269-1281
Laurinavicius, V. et al, Biologija (2003) 31-34
Leung, D. W., et al., Technique 1 (1989) 11-15
Malinauskas, A. et al., Sensors and Actuators, B: Chemical 100 (2004) 395-402
Matsushita, K. and Adachi, O. Bacterial quinoproteins glucose dehydrogenase and alcohol dehydrogenase in "Principles and applications of Quinoproteins" (1993) 47-63, New York, Marcel Dekker
Matsushita, K., et al., Antonie Van Leeuwenhoek 56 (1989) 63-72
Matsushita, K., et al., Biochemistry 28 (1989) 6276-6280
Matsushita, K., et al., Bioscience Biotechnology & Biochemistry 59 (1995) 1548-1555
Olsthoorn, A. J. and Duine, J. A., Arch. Biochem. Biophys. 336 (1996) 42-48
Olsthoorn, A. J. and Duine, J. A., Biochemistry 37 (1998) 13854-13861
Oubrie A., Biochim. Biophys. Acta 1647 (2003) 143-151
Oubrie, A. and Dijkstra, B. W., Protein Sci. 9 (2000) 1265-1273
Oubrie, A., et al., Embo J. 18 (1999) 5187-5194
Oubrie, A., et al., J. Mol. Biol. 289 (1999) 319-333
Oubrie, A., et al., Proc. Natl. Acad. Sci. U.S.A 96 (1999) 11787-11791
Reddy S, and Bruice, T. C., J. Am. Chem. Soc. 126 (2004) 2431-2438
Sambrook, J., et al., in "Molecular Cloning: A Laboratory Manual" (1989)-, Cold Spring Harbour, N.Y., Cold Spring Harbour Laboratory Press
U.S. Pat. No. 5,484,708
U.S. Pat. No. 5,997,817
U.S. Pat. No. 6,057,120
U.S. Pat. No. 6,103,509
Wens, R., et al., Perit. Dial. Int. 18 (1998) 603-609
WO 02/34919
WO 88/09373
Yamada, M. et al., Biochim. Biophys. Acta 1647 (2003) 185-192
Ye, L., et al., Anal. Chem. 65 (1993) 238-241

The invention claimed is:

1. A variant of PQQ-dependent soluble glucose dehydrogenase (s-GDH), said variant comprising the sequence of SEQ ID NO: 2 modified by the insertion of one amino acid residue between the amino acid positions corresponding to positions 428 and 429 of the s-GDH wild-type sequence known from *A. calcoaceticus* (SEQ ID NO: 2), a substitution of threonine at position 348 of SEQ ID NO: 2 with an amino acid residue selected from the group consisting of alanine, glycine and serine, and optionally, one or more additional amino acid substitutions, wherein said variant is at least 90% identical to SEQ ID NO: 2, and has s-GDH activity.

2. The variant according to claim 1 further characterized in that said inserted amino acid is selected from the group consisting of phenylalanine, leucine, methionine and proline.

3. The variant according to claim 1, wherein said inserted amino acid is proline.

4. The variant of PQQ-dependent s-GDH according to claim 1 further characterized in that it comprises at least one amino acid residue substitution at the amino acid position corresponding to position 428 of SEQ ID NO: 2.

5. The variant of PQQ-dependent s-GDH according to claim 4 further characterized in that asparagine at position 428 is substituted with an amino acid residue selected from the group consisting of leucine, proline and valine.

6. A variant according to claim 1 comprising substitutions at both the positions corresponding to positions 348 and 428 of SEQ ID NO: 2.

7. A variant according to claim 1 additionally comprising a substitution at the amino acid position corresponding to position 171 of SEQ ID NO: 2.

8. A variant according to claim 1 additionally comprising a substitution at the amino acid position corresponding to position 245 of SEQ ID NO: 2.

9. A variant according to claim 1 additionally comprising a substitution at the amino acid position corresponding to position 341 of SEQ ID NO: 2.

10. A variant according to claim 1 additionally comprising a substitution at the amino acid position corresponding to position 169 of SEQ ID NO: 2.

11. A variant according to claim 1 additionally comprising a substitution at the amino acid position corresponding to position 349 of SEQ ID NO: 2.

12. A method of detecting, determining or measuring glucose in a sample using a s-GDH variant according to claim 1, said improvement comprising contacting the sample with said variant.

13. The method of claim 12 further characterized in that said detection, determination or measurement of glucose is performed using a sensor or test strip device.

* * * * *

SEQUENCE LISTING

<160> NUMBER OF SEQ ID NOS: 11

<210> SEQ ID NO 1
<211> LENGTH: 1362

<212> TYPE: DNA
<213> ORGANISM: Acinetobacter calcoaceticus
<220> FEATURE:
<221> NAME/KEY: CDS
<222> LOCATION: (1)..(1362)

<400> SEQUENCE: 1

```
gat gtt cct cta act cca tct caa ttt gct aaa gcg aaa tca gag aac    48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cac gcg ttg    96
Phe Asp Lys Lys Val Ile Leu Ser Asn Leu Asn Lys Pro His Ala Leu
            20                  25                  30 tta tgg gga cca gat aat caa att tgg tta act gag cga gca aca ggt   144
Leu Trp Gly Pro Asp Asn Gln Ile Trp Leu Thr Glu Arg Ala Thr Gly
        35                  40                  45 aag att cta aga gtt aat cca gag tcg ggt agt gta aaa aca gtt ttt   192
Lys Ile Leu Arg Val Asn Pro Glu Ser Gly Ser Val Lys Thr Val Phe
    50                  55                  60 cag gta cca gag att gtc aat gat gct gat ggg cag aat ggt tta tta   240
Gln Val Pro Glu Ile Val Asn Asp Ala Asp Gly Gln Asn Gly Leu Leu
65                  70                  75                  80 ggt ttt gcc ttc cat cct gat ttt aaa aat aat cct tat atc tat att   288
Gly Phe Ala Phe His Pro Asp Phe Lys Asn Asn Pro Tyr Ile Tyr Ile
                85                  90                  95 tca ggt aca ttt aaa aat ccg aaa tct aca gat aaa gaa tta ccg aac   336
Ser Gly Thr Phe Lys Asn Pro Lys Ser Thr Asp Lys Glu Leu Pro Asn
            100                 105                 110 caa acg att att cgt cgt tat acc tat aat aaa tca aca gat acg ctc   384
Gln Thr Ile Ile Arg Arg Tyr Thr Tyr Asn Lys Ser Thr Asp Thr Leu
        115                 120                 125 gag aag cca gtc gat tta tta gca gga tta cct tca tca aaa gac cat   432
Glu Lys Pro Val Asp Leu Leu Ala Gly Leu Pro Ser Ser Lys Asp His
    130                 135                 140 cag tca ggt cgt ctt gtc att ggg cca gat caa aag att tat tat acg   480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat   528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat   576
Gln Ala Gln His Thr Pro Thr Gln Gln Glu Leu Asn Gly Lys Asp Tyr
            180                 185                 190 cac acc tat atg ggt aaa gta cta cgc tta aat ctt gat gga agt att   624
His Thr Tyr Met Gly Lys Val Leu Arg Leu Asn Leu Asp Gly Ser Ile
        195                 200                 205 cca aag gat aat cca agt ttt aac ggg gtg gtt agc cat att tat aca   672
Pro Lys Asp Asn Pro Ser Phe Asn Gly Val Val Ser His Ile Tyr Thr
    210                 215                 220 ctt gga cat cgt aat ccg cag ggc tta gca ttc act cca aat ggt aaa   720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc   768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa   816
Ile Val Lys Gly Gly Asn Tyr Gly Trp Pro Asn Val Ala Gly Tyr Lys
            260                 265                 270 gat gat agt ggc tat gct tat gca aat tat tca gca gca gcc aat aag   864
Asp Asp Ser Gly Tyr Ala Tyr Ala Asn Tyr Ser Ala Ala Ala Asn Lys
        275                 280                 285
```

```
tca att aag gat tta gct caa aat gga gta aaa gta gcc gca ggg gtc      912
Ser Ile Lys Asp Leu Ala Gln Asn Gly Val Lys Val Ala Ala Gly Val
    290                 295                 300 cct gtg acg aaa gaa tct gaa tgg act ggt aaa aac ttt gtc cca cca      960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca     1008
Leu Lys Thr Leu Tyr Thr Val Gln Asp Thr Tyr Asn Tyr Asn Asp Pro
                325                 330                 335 act tgt gga gag atg acc tac att tgc tgg cca aca gtt gca ccg tca     1056
Thr Cys Gly Glu Met Thr Tyr Ile Cys Trp Pro Thr Val Ala Pro Ser
            340                 345                 350 tct gcc tat gtc tat aag ggc ggt aaa aaa gca att act ggt tgg gaa     1104
Ser Ala Tyr Val Tyr Lys Gly Gly Lys Lys Ala Ile Thr Gly Trp Glu
        355                 360                 365 aat aca tta ttg gtt cca tct tta aaa cgt ggt gtc att ttc cgt att     1152
Asn Thr Leu Leu Val Pro Ser Leu Lys Arg Gly Val Ile Phe Arg Ile
    370                 375                 380 aag tta gat cca act tat agc act act tat gat gac gct gta ccg atg     1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg     1248
Phe Lys Ser Asn Asn Arg Tyr Arg Asp Val Ile Ala Ser Pro Asp Gly
                405                 410                 415 aat gtc tta tat gta tta act gat act gcc gga aat gtc caa aaa gat     1296
Asn Val Leu Tyr Val Leu Thr Asp Thr Ala Gly Asn Val Gln Lys Asp
            420                 425                 430 gat ggc tca gta aca aat aca tta gaa aac cca gga tct ctc att aag     1344
Asp Gly Ser Val Thr Asn Thr Leu Glu Asn Pro Gly Ser Leu Ile Lys
        435                 440                 445 ttc acc tat aag gct aag                                             1362
Phe Thr Tyr Lys Ala Lys
    450

<210> SEQ ID NO 2
<211> LENGTH: 454
<212> TYPE: PRT
<213> ORGANISM: Acinetobacter calcoaceticus

<400> SEQUENCE: 2

Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140
```

-continued

```
Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
            165                 170                 175

Gln Ala Gln His Thr Pro Thr Gln Gln Glu Leu Asn Gly Lys Asp Tyr
        180                 185                 190

His Thr Tyr Met Gly Lys Val Leu Arg Leu Asn Leu Asp Gly Ser Ile
    195                 200                 205

Pro Lys Asp Asn Pro Ser Phe Asn Gly Val Val Ser His Ile Tyr Thr
210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Glu Ile Asn Leu
            245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Asn Lys
            275                 280                 285

Ser Ile Lys Asp Leu Ala Gln Asn Gly Val Lys Val Ala Ala Gly Val
            290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
            355                 360                 365

Asn Thr Leu Leu Val Pro Ser Leu Lys Arg Gly Val Ile Phe Arg Ile
    370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Asn Val Gln Lys Asp
            420                 425                 430

Asp Gly Ser Val Thr Asn Thr Leu Glu Asn Pro Gly Ser Leu Ile Lys
        435                 440                 445

Phe Thr Tyr Lys Ala Lys
    450
```

<210> SEQ ID NO 3
<211> LENGTH: 29
<212> TYPE: DNA
<213> ORGANISM: Artificial
<220> FEATURE:
<223> OTHER INFORMATION: Primer sequence for T348G sense strand

<400> SEQUENCE: 3
catttgctgg ccaggggttg caccgtcat                              29

<210> SEQ ID NO 4
<211> LENGTH: 29
<212> TYPE: DNA
<213> ORGANISM: Artificial
<220> FEATURE:

<223> OTHER INFORMATION: Primer sequence for T348G antisense strand

<400> SEQUENCE: 4
atgacggtgc aaccccctggc cagcaaatg        29

<210> SEQ ID NO 5
<211> LENGTH: 20
<212> TYPE: DNA
<213> ORGANISM: Artificial
<220> FEATURE:
<223> OTHER INFORMATION: Sequencing primer GDH 1

<400> SEQUENCE: 5
ttaacgtgct gaacagccgg        20

<210> SEQ ID NO 6
<211> LENGTH: 20
<212> TYPE: DNA
<213> ORGANISM: Artificial
<220> FEATURE:
<223> OTHER INFORMATION: Sequencing primer GDH 2

<400> SEQUENCE: 6
atatgggtaa agtactacgc        20

<210> SEQ ID NO 7
<211> LENGTH: 27
<212> TYPE: DNA
<213> ORGANISM: Artificial
<220> FEATURE:
<223> OTHER INFORMATION: Wobbled insertion primer  in429X_F sense strand
<220> FEATURE:
<221> NAME/KEY: misc_feature
<222> LOCATION: (12)..(14)
<223> OTHER INFORMATION: n is a, c, g, or t

<400> SEQUENCE: 7
ctgccggaaa tnnngtccaa aaagatg        27

<210> SEQ ID NO 8
<211> LENGTH: 27
<212> TYPE: DNA
<213> ORGANISM: Artificial
<220> FEATURE:
<223> OTHER INFORMATION: Wobbled insertion primer  in429X_R anti sense
      strand
<220> FEATURE:
<221> NAME/KEY: misc_feature
<222> LOCATION: (14)..(16)
<223> OTHER INFORMATION: n is a, c, g, or t

<400> SEQUENCE: 8 catcttttttg gacnnnattt ccggcag        27

<210> SEQ ID NO 9
<211> LENGTH: 28
<212> TYPE: DNA
<213> ORGANISM: Artificial
<220> FEATURE:
<223> OTHER INFORMATION: insP429

<400> SEQUENCE: 9
gatactgccg gaaatccagt ccaaaaag        28

<210> SEQ ID NO 10
<211> LENGTH: 28
<212> TYPE: DNA

```
<213> ORGANISM: Artificial
<220> FEATURE:
<223> OTHER INFORMATION: insP429_R

<400> SEQUENCE: 10 cttttggac tggtcctccg gcagtatc                                               28

<210> SEQ ID NO 11
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 11

Gly Asn Xaa Val Gln Lys Asp
1               5
```